United States Patent [19]

Demarne et al.

[11] Patent Number: 4,587,245
[45] Date of Patent: May 6, 1986

[54] METHOD OF TREATING NEUROPSYCHIC DISTURBANCES BY BENZODIAZEPINE DERIVATIVES AND COMPOSITION THEREFOR

[75] Inventors: Henri Demarne, Montpellier; André Hallot, Saint-Gely-Du-Fesc, both of France

[73] Assignee: Sanofi, Paris, France

[21] Appl. No.: 695,557

[22] Filed: Jan. 28, 1985

Related U.S. Application Data

[60] Continuation-in-part of Ser. No. 545,588, Oct. 26, 1983, abandoned, which is a continuation of Ser. No. 170,748, Jul. 21, 1980, abandoned, which is a continuation of Ser. No. 015,466, Feb. 26, 1979, abandoned, which is a division of Ser. No. 794,243, May 5, 1977, abandoned.

[30] Foreign Application Priority Data

May 5, 1976 [GB] United Kingdom ............... 18492/76

[51] Int. Cl.$^4$ ............................................. A61K 31/55
[52] U.S. Cl. ............................. 514/221; 260/239.3 D
[58] Field of Search ................. 260/239.3 D; 514/221

[56] References Cited

U.S. PATENT DOCUMENTS

| Re. 28,315 | 1/1975 | Schmitt | 260/239.3 D |
| 3,516,988 | 6/1970 | Schmitt | 260/239.3 D |
| 3,657,223 | 4/1972 | Hellerbach et al. | 260/239.3 D |

FOREIGN PATENT DOCUMENTS 684601 7/1968 South Africa ............... 260/239.3 D

OTHER PUBLICATIONS

Culvenor "Amine Oxides" in Reviews of Pure and Applied Chemistry, vol, 3, pp. 83–114 (1953).
Sternbach et al., "Some Aspects of Structure–Activity Relationship in Psychotropic Agents of the 1,4-Benzodiazepine Series (A Symposium held at the Regional Research Laboratory, Hyderbad (India) (1966).

Primary Examiner—Robert T. Bond
Attorney, Agent, or Firm—Stevens, Davis, Miller & Mosher

[57] ABSTRACT

Benzodiazepines of formula

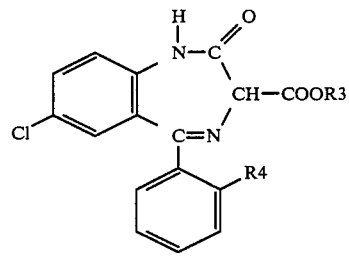

wherein R3 is methyl or ethyl and R4 is chlorine or fluorine are useful therapeutic agents for the treatment of neuropsychic disturbances.

11 Claims, No Drawings

METHOD OF TREATING NEUROPSYCHIC DISTURBANCES BY BENZODIAZEPINE DERIVATIVES AND COMPOSITION THEREFOR

CROSS REFERENCES TO RELATED APPLICATIONS

This is a continuation-in-part of our copending application Ser. No. 545,588 of Oct. 26, 1983 which is a continuation of the application Ser. No. 170,748 of July 21, 1980 which is a continuation of the application Ser. No. 15,466 of Feb. 26, 1979 which is a division of the application Ser. No 794,243 of May 5, 1977, all now abandoned.

FIELD OF THE INVENTION

The present invention relates to a method for the treatment of patients subject to neuropsychic disturbances without inducing sedation by administration of a benzodiazepine derivative.

DESCRIPTION OF THE PRIOR ART

The family of the benzodiazepines has been described over the course of many years, for example in French patent No. 1,497,456, corresponding to U.S. Pat. Nos. 3,516,988 and Re 28,315, and the action on the central nervous system of certain members of this family has also been described.

The U.S. Pat. No. 3,657,223 discloses and claims a chemical process for the preparation of benzodiazepines by enlarging a six-member heterocyclic ring. Among a broad series of benzodiazepines, the 7-chloro-3-ethoxycarbonyl-5-(2-fluorophenyl)-2-oxo-2,3-dihydro-1H-1,4-benzodiazepine and the 7-chloro-5-(2-chlorophenyl)-3-ethoxycarbonyl-2-oxo-2,3-dihydro-1H-1,4-benzodiazepine have been described in the above patent; however, no mention of the pharmacological properties of these two compounds has been made.

The continuation of the studies relating to the various products of the said family and also of related products has made it possible to show the interesting specific properties of certain sub-families of benzodiazepines. It is this which is the subject of the present invention.

SUMMARY OF THE INVENTION

It has now been found that a therapeutically effective amount of a benzodiazepine derivative of formula

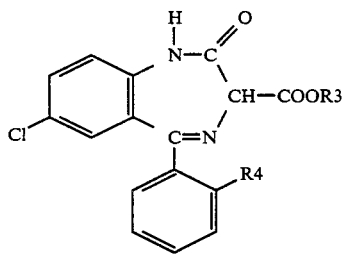

(I)

wherein R3 is methyl or ethyl and R4 is chlorine or fluorine, may be administered to a patient suffering from psychic disturbances, in particular anxiety, in order to relief said disturbances.

It has also been found that, despite their high pharmacological activity, the benzodiazepines of formula (I) have a relatively poor affinity for the benzodiazepine receptors.

It has further been found that the benzodiazepines of formula (I) above, when administered in a primate, assure a continuous release of metabolites having an high affinity for the benzodiazepine receptors.

It has finally been found that the benzodiazepines of formula (I) above show an unexpected dissociation between the anxiolytic and sedative activities and that they can be used for the relief of psychic disturbances without causing sedation.

DETAILED DESCRIPTION

Thus, it is an object of the present invention to provide a method for the treatment of a patient subject to neuropsychic disturbances which comprises administering to said patient a therapeutically effective amount of a benzodiazepine derivative of formula (I) above in admixture with a pharmaceutical carrier.

Said neuropsychic disturbances include anxiety, reactive depressive conditions and anxiety neuroses.

The active principle will be presented in appropriate forms for oral, parenteral or endorectal administration, for example drops, syrups, granules, cachets, pills, suppositories or injectable solutions.

The posology, which varies in accordance with the afflictions to be treated and the age of the patient, can vary from 2 mg to 100 mg per day.

It is another object of the present invention to provide a pharmaceutical composition for the treatment of neuropsychic disturbances comprising an effective amount of a compound selected from the group consisting of the benzodiazepine derivatives of formula (I) above in admixture with a pharmaceutical carrier.

The pharmaceutical compositions, which are in dosage unit form, contain from 0.1 to 25 mg of active ingredient, preferably about 2 mg, and may be administered to the patient to be treated once to four times per day.

Generally, a tablet or capsule containing 2 mg of active ingredient can be administered orally once a day to control anxiety without inducing sedation.

The benzodiazepine derivatives of formula (I) can, in principle, be prepared by employing the process described earlier, in French Patent No. 1,497,456; unfortunately, this process does not make it possible to obtain the said products in acceptable yield and acceptable purity so that hitherto it has not been possible to test the pharmacological properties of these products.

To prepare the products according to the invention in a high yield, it is possible to use one of the two following methods.

The first method, represented in scheme 1, consists of closing the diazepine ring by forming the 1,2-amide bond.

Scheme 1

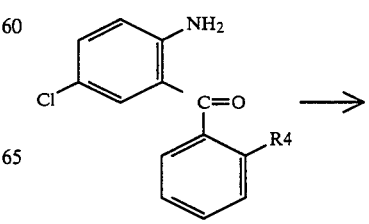

-continued
Scheme 1

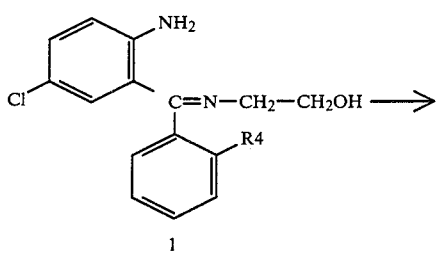

1

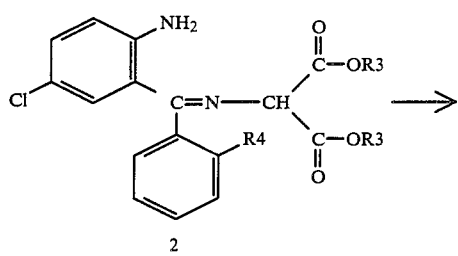

2

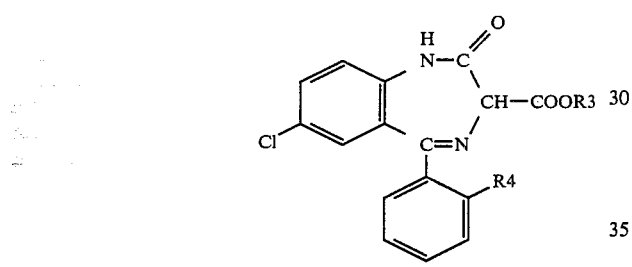

The imine 1 is formed from the suitably substituted benzophenone by reaction with excess ethanolamine at the reflux temperature in the presence of a hydrochloride of a tertiary amine or of 2-methylimidazole hydrochloride.

This imine is reacted with the hydrochloride of a dialkyl aminomalonate in an alcohol and in the presence of acetic acid, to give the substituted imine 2.

Finally, the imine 2 is cyclised to give the benzodiazepine by heating in acetic acid.

The second method, represented in scheme 2, consists of closing the diazepine ring by forming the 4,5-imine bond.

Scheme 2

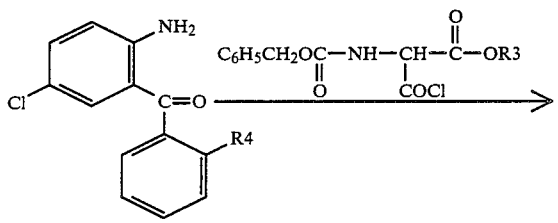

-continued
Scheme 2

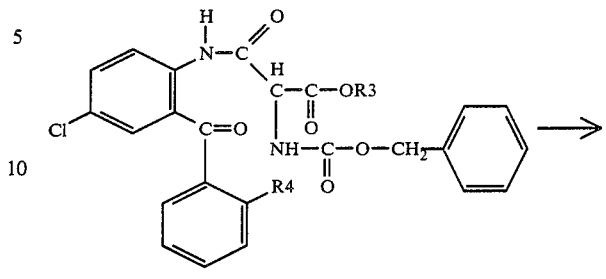

3

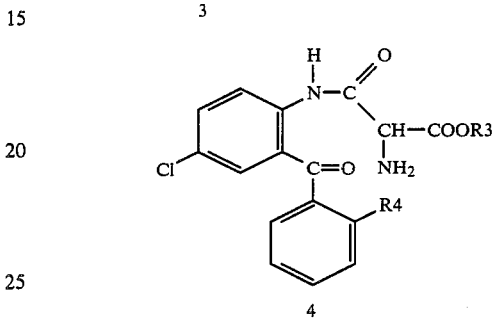

4

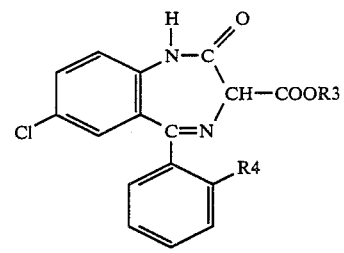

The first step consists of condensing an orthoaminobenzophenone with the acid chloride of the monoalkyl N-carbobenzyloxyaminomalonate. The reaction is carried out at a low temperature (−20° to 0° C.) and yields the amide 3. The latter yields the amine compound 4 in an anhydrous acid medium (acetic acid or hydrobromic acid dissolved in ethyl acetate) at between 20° and 50° C. This amine compound is cyclised to give the benzodiazepine by heating under reflux in acetic acid.

The non-limiting examples which follow illustrate the invention.

EXAMPLE 1

7-chloro-3-ethoxycarbonyl-5-(2-fluorophenyl)-2-oxo-2,3-dihydro-1H-benzodiazepine-1,4

(R3=C2H5, R4=F)

Code No.: CM 6912.

(a) 1-(2-amino-5-chlorophenyl)-1-(2-fluorophenyl)-2-azabut-1-en-4-ol

A mixture of 40 g of 2-methylimidazole hydrochloride and of 90 g of 2-amino-5-chloro-2'-fluoro-benzophenone in 240 ml of ethanolamine is heated at 135° for 2 hours. After cooling, the reaction mixture is poured into an aqueous sodium bicarbonate solution. The mixture is extracted with ether, the organic phase is washed repeatedly with water and is dried over sodium sulphate, and the solvent is evaporated to dryness. The residual oil is chromatographed on a silica column, elution being carried out with a 50/50 mixture of cyclohexane and ethyl acetate.

88 g of the expected imine are thus isolated. Melting point: 105°–110° C.

(b) 1-(2-amino-5-chlorophenyl)-1-(2-fluorophenyl)-3,3-bis-(ethoxycarbonyl)-2-aza-prop-1-ene A mixture of 88 g of the product obtained above, 300 g of ethyl aminomalonate hydrochloride and 60 ml of acetic acid in 2.3 liters of absolute ethanol is heated to the reflux temperature for 6 hours. The alcohol and the acetic acid are evaporated in vacuo and the residue is taken up in ether. The solution is washed with a dilute sodium bicarbonate solution and then with water and is dried over sodium sulphate. The solvent is evaporated and the residue is then chromatographed on a silica column, using a 90/10 mixture of chloroform and ethyl acetate for the elution. An oil (64 g) is thus obtained, and is used, without further treatment, for the cyclisation. A sample recrystallised from isopropyl ether has a melting point of 119° C.

(c) Compound of Code No CM 6912

25 g of the imine obtained under (b), dissolved in 400 ml of acetic acid, are heated at the reflux temperature for 1 hour. After evaporating the solvent in vacuo, the residue is taken up in methylene chloride. The solution is washed with a dilute sodium bicarbonate solution and then with water. After evaporating the solvent, the residue is chromatographed on silica, elution being carried out with an 80/20 mixture of ether and ethyl acetate. 9 g of benzodiazepine are thus obtained. Melting point: 196° C.

EXAMPLE 2

7-chloro-3-ethoxycarbonyl-5-(2-chlorophenyl)-2-oxo-2,3-dihydro-1H-benzodiazepine-1,4

($R_3 = C_2H_5$, $R_4 = Cl$)
Code No.: CM 7101
(a) Preparation of compound 3
$R_3 = C_2H_5$, $R_4 = Cl$ 52 g of monoethyl benzyloxycarbonylamonimalonate are suspended in 300 ml of methylene chloride and the suspension is cooled to $-20°$ C. 40 g of phosphorus pentachloride are added slowly, whilst stirring, in such a way that the temperature remains between $-15°$ and $-20°$ C. Thereafter 50 g of 2-amino-2',5-dichloro-benzophenone are added at between $-10°$ and $-20°$ C. When the addition is completed, the temperature is again allowed to rise to 0° C., after which 300 ml of a 10% strength sodium carbonate solution are added. The mixture is again stirred for 30 minutes and the organic phase is then separated off, washed with water and then dried over sodium sulphate.

The solvent is evaporated to dryness and an oil (90 g) consisting of the compound 3 is obtained, which is used, without further treatment, for the following stage.
(b) Preparation of compound 4
$R_3 = C_2H_5$, $R_4 = Cl$ 69 g of the above compound are dissolved in 150 ml of ethyl acetate and a solution of 50 g of hydrogen bromide gas in 150 ml of ethyl acetate is then added at a temperature of between 0° and +10° C. The reaction mixture is heated at 50° C. until the evolution of carbon dioxide has ceased (about 30 minutes) and is then poured, whilst stirring, into a mixture comprising 60 ml of concentrated ammonia, 100 ml of water and 200 g of crushed ice. The batch is extracted with ether and the ether solution is washed 3 times with water and is dried over sodium sulphate. After evaporating the solvent at 50° in vacuo, the residue is triturated with 2 liters of pentane to remove the benzyl bromide formed during the reaction.

The residue, consisting of the compound 4, is used, without further treatment, for the cyclisation stage.
(c) Compound of Code No CM 7101

The compound 4 obtained above is taken up in 400 ml of acetic acid and the solution is heated under reflux for 1 hour. After cooling, the reaction mixture is poured into 600 ml of concentrated ammonia to which 400 g of crushed ice have been added. A solid separates out, and is filtered off, washed with water and then with pentane, and recrystallised from methanol.

23 g of benzodiazepine (CM 7101) are thus obtained. Melting point: 152° C.

Using the same process but replacing the monoethyl benzoyloxycarbonylaminomalonate by monoethyl benzoyloxycarbonylaminomalonate as the reactant in the preparation of compound 3, the product of code number 7442 is prepared, in which $R_3 = CH_3$ and $R_4 = Cl$. This product has a melting point of 224° C.

EXAMPLE 3

Pills:
CM 6912: 2 mg
talc: 113 mg

EXAMPLE 4

Tablets:
CM 6912 or 7101: 2 mg
lactose: 71 mg
microcystalline cellulose: 45 mg
Mg stearate: 2 mg The products according to the invention were subjected to pharmacological tests in mice in order to determine their activity on the central nervous system. We shall indicate below the various tests to which the products were subjected.

In all cases the products were administered orally.

1. Spontaneous actography

The animals are placed in individual cages through which pass two beams which strike two photoelectric cells.

During their movements, the animals (mice) intercept the beams and cause a recording on the impulse counters.

The variations in the motility of the treated animals are expressed in percentages relative to comparison animals; the sign-indicates a reduction (in percent) of the motility of the subjects.

2. Traction test

This consists of observing whether the animals (mice) are capable of pulling themselves up on a horizontal bar gripped by the front paws.

This test demonstrates a sedative effect or a relaxing effect on the striped muscle.

The results are expressed as the 50% effective dose (ED50), which is the dose (in mg/kg) for which 50% of the mice can no longer pull themselves up.

3. Rotating rod test: equilibration

Normal animals (mice) placed on a horizontal rod subjected to a rotational movement do not fall.

This test demonstrates the equilibration faculties of the normal animal, which disappear or are reduced in subjects which have been rendered ataractic.

The results are expressed as the 50% effective dose (ED50) which is the dose (in mg/kg) for which 50% of the mice fall during the test.

Anti-convulsive activity in relation to cardiazol

When administered intraperitoneally at a dose of 125 mg/kg, pentylenetetrazol (or cardiazol) causes the appearance of lethal convulsions in 100% of the mice treated.

The active products administered orally prior to the cardiazol oppose the appearance of the convulsions and possibly allow the test animals to survive.

The results are expressed as the ED50, that is to say as the dose (in mg/kg) which protects 50% of the animals.

Anti-convulsive activity in relation to electric shock

An alternating current of 12.5 V is applied for 0.5 second by means of corneal electrodes to batches of 12 mice treated 1 hour beforehand with the product to be studied. The untreated mice subjected to this electric shock undergo a convulsion of the tonic type. For the treated mice, the number of mice which do not undergo a convulsion is noted and a percentage protection against convulsion is thus obtained.

The result is expressed as the 50% effective dose (ED50) which is the dose (in mg/kg) for which 50% of the mice do not undergo a convulsion.

Anxiolytic activity: 4 plate test

The device is a parllelopiped chamber of which the floor consists of 4 metal plates of equal area. The experimenter can create a difference of potential which corresponds to a current of intensity 0.35 mA for a duration of 0.2 second, between each plate. Each time a mouse passes from one plate to the other, it receives an electric shock.

The anxiolytic agents cause an indifference to these electric shock and as a result the treated mice cross from one plate to another more frequently than the comparison mice. 45 minutes after administration of the product to be studied, the mice are placed in the chamber for 1 minute and the number of shocks received is measured and compared with the number of shocks received by the comparison animals. The results are expressed as a percentage increase in the number of shocks received by the treated animals relative to the comparison animals (which amounts to a percentage effect for a given dose), or as a threshold dose (TD) which is the lowest dose which produces a significant effect.

Toxicity

Finally, for certain products, the LDo in mg/kg (for oral administration) has been provided.

The results obtained in these various test are summarised in the table below. In this table are shown, by way of comparison product, the results obtained with a related product which however does not belong to the family of the present invention; this product was given the code number CM 4279; it is a benzodiazepine of the formula (I) in which R3 is C2H5 and R4 is H.

TABLE

| Product | Toxicity LD. mg/kg | Motor characteristics | | | | Anti-convulsive action | | Anxiolysis 4 plates |
|---|---|---|---|---|---|---|---|---|
| | | Actography | | Traction $ED_{50}$ mg/kg | Equilibration $ED_{50}$ mg/kg | Cardiazol $ED_{50}$ mg/kg | Electric shock $ED_{50}$ mg/kg | |
| | | dose mg/kg | % | | | | | |
| 6912 | >300 | 33 | −23 | 10 | 5 | 0.6 | 12 | TD 1 |
| 7101 | >300 | 0.5 | −58 | 6 | 6 | 0.75 | 12 | TD 0.5 |
| 7442 | >300 | 0.5 | −57 | 5 | 8 | 0.4 | 32 | TD 0.1 |
| 4279 | >300 | 100 | none | 100 | >100 | 9 | >500 | TD 10 |

Dissociation of the anxiolytic and sedative activities

Male Wistar rats are trained in Skinner boxes (Campden) in an approach-avoidance conflict procedure (Davidson and Cook, Psychopharmacologia 1969, 15, 159). The session lasts 30 minutes and consists of a multiple VI 30 sec/FR 3 schedule (sequence: 10 minutes VI+2 minutes FR+10 minutes VI+2 minutes FR+6 minutes VI). During the conflict periods, signalled by a light cue every 3d press delivers simultaneously a pellet and an electric shock. The shock intensity is titrated to each animal sensitivity so that rats do not press the lever more than 6 times per session. Lever presses are authomatically recorded by a microcomputer: non punished responses during the VI schedule and punished responses during the FR periods. A representative benzodiazepine of formula (I) above (R3=ethyl, R4=F; Code No. CM 6912) has been injected by intraperitoneal route 30 minutes before the test.

In this test, which allows the measure—in the same rat—of both antianxiety (increase in punished responding) and sedation (decrease in unpunished responding), the compound CM 6912 shows anxiolytic activity with an ED50 of 1.66 mg/kg and a sedative activity with an ED50 of 16 mg/kg. The dissociation of the anxiolytic and sedative activities is statistically significant.

Mechanism of action

Therapeutic evaluation of a representative benzodiazepine derivative of formula I (R3=ethyl, R4=F; Code No. CM 6912) in man revealed potent anxiolytic properties at a daily dosage of 2 mg without adverse effect.

For this purpose, a pharmaceutical composition containing 2 mg of CM 6912 is administered once a day.

The originality of the mechanism of action of CM 6912 has been determined by the appearance profile of active metabolites after oral administration.

Several studies of drug disposition of CM 6912 in several animal species and in man showed that this compound is stable in the gastro-intestinal tract and is biotransformed into the free acid (formula (I), R3=H, R4=F). The free acid, which is an inactive metabolite, acts as a reservoir from which active metabolites, unsubstituted in the 3-position and hydroxylated in the 3-position, are progressively formed. The active metabolites do not show a peak in their appearance profile.

Studies were performed in mice and rats in order to evaluate the respective affinities of CM 6912 and of its metabolites on the central receptor site of the benzodiazepines. CM 6912 and the corresponding free acid were found weak displacers of 3H-flunitrazepam in vitro whereas the de-carbethoxy and the 3-hydroxy analogs, the active metabolites, were found very potent.

This mechanism of action, which is quite unexpected and unique in the benzodiazepine series, and the property of dissociating the anxiolytic and sedative activities in favour of the former, render the benzodiazepine derivatives of formula (I) above qualitatively different from all the known benzodiazepine drugs.

What we claim is:

1. A method for the treatment of a patient subject to neuropsychic disturbances which comprises administering orally to said patient an effective therapeutic dose of a compound of formula

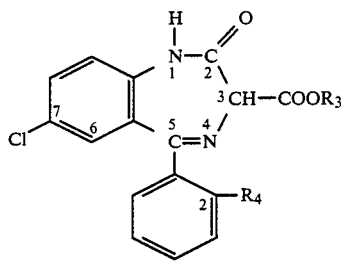

wherein R3 is methyl or ethyl and R4 is chlorine or fluorine; said compound being present in an amount sufficient to bring about an anxiolytic effect but without inducing significant sedation.

2. A method as claimed in claim 1 in which the effective therapeutic dose of said compound is of from 2 to 100 mg per day.

3. A method as claimed in claim 1 or 2 in which said compound is 7-chloro-3-ethoxycarbonyl-5-(2-fluorophenyl)-2-oxo-2,3-dihydro-1H-1,4-benzodiazepine.

4. A method as claimed in claim 1 or 2 in which said active compound is 7-chloro-5-(2-chlorophenyl)-3-ethoxycarbonyl-2-oxo-2,3-dihydro-1H-1,4-benzodiazepine.

5. An oral pharmaceutical composition in dosage unit form for the control of anxiety without inducing significant sedation which comprises about 2 mg per dosage unit of a compound of formula

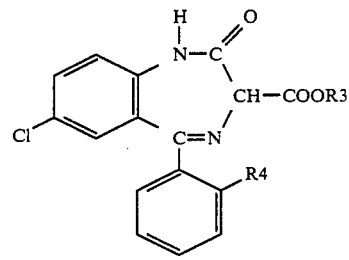

wherein R3 is methyl or ethyl and R4 is fluorine or chlorine, in admixture with a pharmaceutical carrier.

6. A composition as claimed in claim 5 in which said compound is 7-chloro-3-ethoxycarbonyl-5-(2-fluorophenyl)-2-oxo-2,3-dihydro-1H-1,4-benzodiazepine.

7. A composition as claimed in claim 5 in which said compound is 7-chloro-5-(2-chlorophenyl)-3-ethoxycarbonyl-2-oxo-2,3-dihydro-1H-1,4-benzodiazepine.

8. A method for the treatment of a patient subject to neuropsychic disturbances comprising the administration orally of a pharmacuetical composition comprising a compound of the formula:

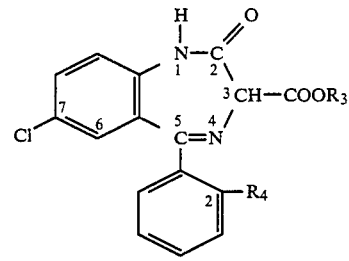

wherein $R_3$ is selected from the group consisting of methyl and ethyl and $R_4$ is a halogen atom selected from the group consisting of chlorine and fluorine, in association with a pharmaceutically acceptable inert carrier, said compound being present in the composition in an amount effective for the treatment of neuropsychic disturbances without inducing significant sedation, and wherein the neuropsychic disturbance-countering dose is from 2 mg to 100 mg per day.

9. A method as in claim 8, wherein $R_3$ is ethyl and $R_4$ is fluorine.

10. A method as in claim 8, wherein $R_3$ is ethyl and $R_4$ is chlorine.

11. A method as in claim 8, wherein the inert carrier is talc.

* * * * *